US00PP11527P

United States Patent [19]

Twomey

[11] Patent Number: Plant 11,527

[45] Date of Patent: Sep. 26, 2000

[54] HYBRID TEA ROSE PLANT NAMED 'TWOAT'

[76] Inventor: Jerry Twomey, 194 Avocado St., Leucadia, Calif. 92024

[21] Appl. No.: 09/220,901

[22] Filed: Dec. 24, 1998

[51] Int. Cl.[7] ..... A01H 5/00

[52] U.S. Cl. ..... Plt./137

[58] Field of Search ..... Plt./137, 130, 138

[56] References Cited

U.S. PATENT DOCUMENTS

P.P. 8,631 3/1994 Tulp ..... Plt./137
P.P. 8,910 9/1994 Davidson ..... Plt./137

*Primary Examiner*—Howard J. Locker

[57] ABSTRACT

A new rose cultivar of the Hybrid Tea class characterized by having Camelia like pink flowers with light sweet perfume. Very uniform bush 100 to 150 cm in height with early and continous blooming. This plant has been designated as 'Twoat'.

1 Drawing Sheet

The present invention relates to a new and distinctive cultivar of rose plant of the Hybrid Tea class, which was originated by my crossing 'Evening Star' as the seed parent with Marijke Koopman as pollen parent.

Among the novel characteristics possessed by the new cultivar which distinguish it from:

(a) All other cultivars of which I am aware are: (1) Lightly fluted camelia-like flowers. (2) Very early and free blooming. (3) High degree of disease resistance. (4) Does extremely well on its own roots.

(b)

*Seed parent.*—White flowered, Hybrid Tea.

*Pollen parent.*—Medium pink cluster flowers, Hybrid Tea.

Asexual reproduction of the new rose cultivar by budding, as performed at Wasco, Calif. shows that the aforementioned and all other distinctive characteristics come true to form and are established and transmitted through succeeding propagations.

The accompanying drawing shows typical specimens of the vegetative growth and flowers of the new cultivar in different stages of development and as depicted in color as nearly true as it is reasonably possible to make the same in a color illustration of this character.

The following is a detailed description of my new cultivar, with color terminology in accordance with The Royal Horticultural Society Colour Chart (R.H.S.C.C.). The terminology used in the color description herein refers to plate numbers in the aforementioned color chart, e.g. "53A" is plate "53A" of The Royal Horticultural Society Colour Chart.

Parentage:

*Seed parent.*—'Evening Star', U.S. Plant Pat. No. 3,432.

*Pollen parent.*—'Marijke Koopman', not patented.

Class: Hybrid Tea.

The following observations are made of specimens grown outdoors in Monterey County, Calif., in the month of August, 1998.

FLOWER

Blooming habit:

A. Bud:

(1) *Size.*—Sepals enclosed, 22–24 mm from base of sepals to top of bud.

(2) *Form.*—High Centered.

(3) *Sepals.*—27 to 29 mm in length; 5 to 7 mm extension beyond bud; no serration shown on sepal edges. Generally 3 out of 5 sepals show appendages on each side, 4 to 8 mm length. Sepals show glandular development on edges. Heavy cotton matting on inner surface, fine matting on outer surface. Outside color 147C; inside 183B.

(4) *Peduncle.*—Length — 6 to 6.5 cm. Surface — smooth, no prickles, a few glandular hairs, Strength — firm. Color — 146B and somewhat suffused with reddish coloration.

(5) *Receptacle.*—Shape round, 11–12 mm diameter, Color — 146B.

(6) *Color.*—When sepals first divide, outside bud petals near to 55C.

B. Bloom:

(1) *Size.*—When open — 12 to 13 cm.

(2) *Borne.*—About 3 per stem.

(3) *Form.*—Fluted, exposed center when fully open.

(4) *Petalage.*—Average — 24 to 28.

(5) *Color.*—Early open: outer side of petals 55C; base of petals 10A. Inner petals near 55C with shades of 55B, base near 10C. Aging: near 56A with shades of 56B and base of 10C.

C. Petals:

(1) *Texture.*—Firm.

(2) *Appearance.*—Flexed; satiny.

(3) *Form.*—High center.

(4) *Arrangement.*—Symmetrical.

(5) *Petaloids in center.*—Average 4 to 6.

(6) *Persistence.*—Good, self cleaning.

(7) *Fragrance.*—Light, sweet.

(8) *Lasting quality.*—On plant 7; cut 6 days.

REPRODUCTIVE ORGANS

A. Stamen:

(1) *Arrangement.*—Regular around styles.

(2) *Number.*—Average 180–190.

(3) *Length.*—Average — 8 to 12 mm.
(4) *Filaments.*—Close — Close to 21D.
(5) *Anthers.*—Close — Close to 22A.
(6) *Pollen.*—Close to 22B.

B. Pistil:
(1) *Styles.*—Length: 3–4 mm exposed; number: 80 to 90; color: near to 9C; sparsely coated with white hairs.
(2) *Stigma.*—Color — Close to 46B.
(3) *Ovary.*—Shape — round; 9–10 mm center crossection at sepal base.

C. Hips: Does not set seed.

PLANT

A. Form: Full upright bush.
B. Growth: Very Vigorous; Height: average 1 to 1½ meter.
C. Stem length: Basal break to flower bud tip: average — 1 to 1⅓ m.
D. Foliage: Compound of 3 to 5 leaflets on bloom stem; 5 to 7 leaflets on main canes.
(1) *Mature size.*—5 leaflet — tip of leaflet to stipule base 16–17 cm.
(2) *Quantity.*—Stems well covered.
(3) *Color.*—New foliage upper side close to 146A; under side near 146B. Old foliage upper side near to 147A, under side near to 147B.
(4) *Shape.*—Oval with center pointed.
(5) *Texture.*—Firm, leathery, slightly glossy.
(6) *Edge.*—Little serration on outer edge. Average 3 points per 1 cm, with up to 1 mm peak.
(7) *Rachis.*—Few glandular hairs on upper side; lower side none. Few prickles 2 mm length, spaced near to 4 mm apart.
(8) *Stipules.*—Length 3–3.5 cm; auricle to 8–10 mm. Edge of stipule to tip of auricle with many glandular hairs.

E. Resistance to disease: Very good on powdery mildew, rust and blackspot.
F. Wood:
*New wood.*—Color close to 138A, Bark — smooth.
*Old wood.*—Color close to 146A; Bark — smooth.
G. Thorns on mature wood:
*Size.*—8 to 10 mm.
*Number per* 10 *cm.*—Primary wood 3–4 thorns; Secondary wood same.
*Shape.*—Hooked.
*Color.*—Early stage close to 176D; Aging close to 176B.
H. Winter hardiness: Good.

I claim:

1. A new and distinct rose cultivar of the hybrid tea class, substantially as herein shown and described.

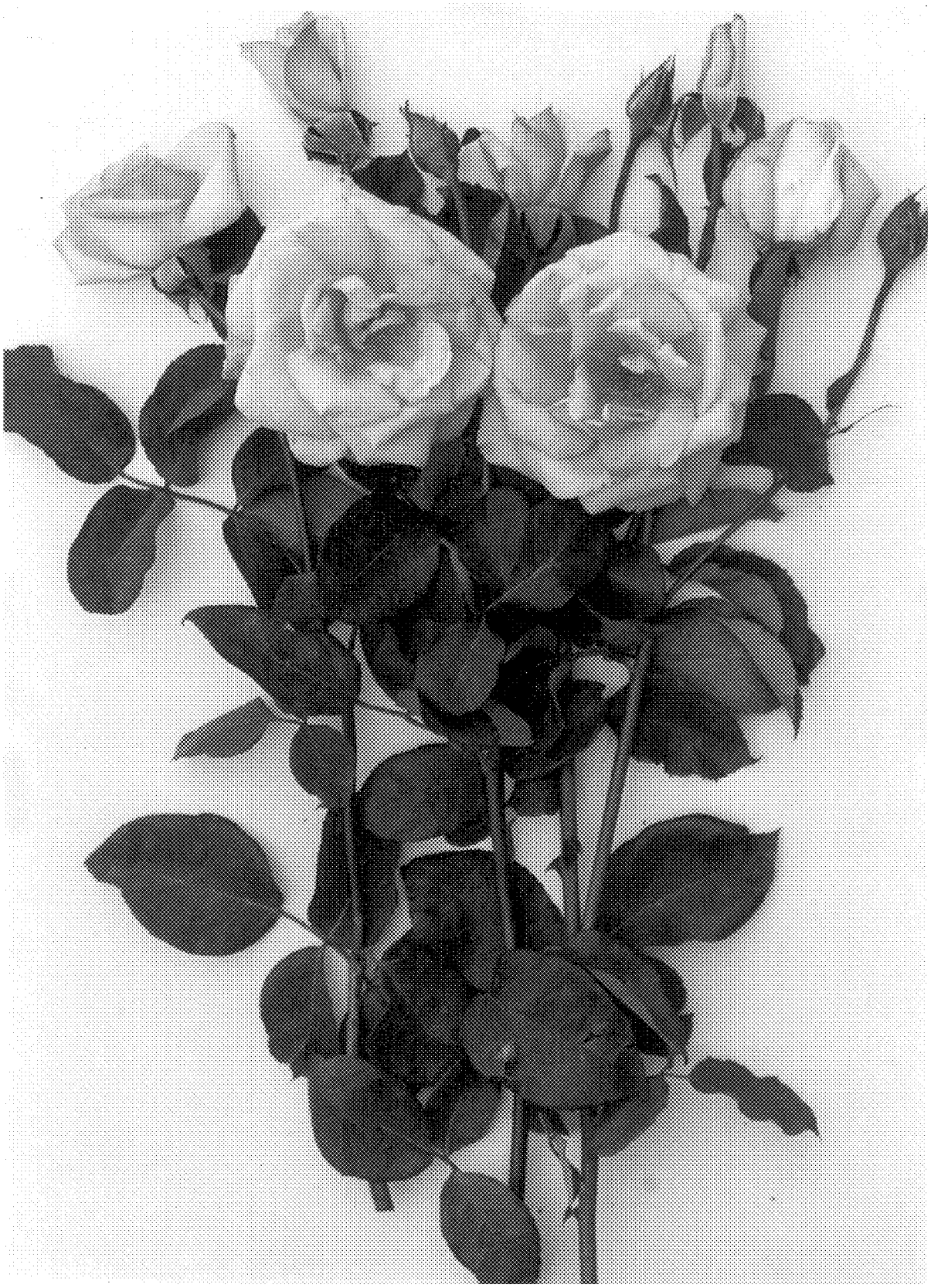

* * * * *